United States Patent
Yamashita

(10) Patent No.: US 12,201,816 B2
(45) Date of Patent: Jan. 21, 2025

(54) HYDROGEN PEROXIDE SOLUTION-PREFILLED SYRINGE WITH EXCELLENT HYDROGEN PEROXIDE PRESERVATION DUE TO SILICONE OIL INCLUDED IN OIL COMPOSITION

(71) Applicant: KORTUC Inc., Chiyoda-ku (JP)

(72) Inventor: Shogo Yamashita, Tokyo (JP)

(73) Assignee: KORTUC Inc., Chiyoda-ku (JP)

( * ) Notice: Subject to any disclaimer, the term of this patent is extended or adjusted under 35 U.S.C. 154(b) by 0 days.

(21) Appl. No.: 16/936,199

(22) Filed: Jul. 22, 2020

(65) Prior Publication Data

US 2020/0345938 A1 Nov. 5, 2020

Related U.S. Application Data

(63) Continuation of application No. PCT/JP2020/014110, filed on Mar. 27, 2020.

(51) Int. Cl.
| | |
|---|---|
| *A61M 5/31* | (2006.01) |
| *A61K 33/40* | (2006.01) |
| *A61K 41/00* | (2020.01) |
| *A61M 5/32* | (2006.01) |
| *C03C 17/30* | (2006.01) |
| *C09D 183/04* | (2006.01) |

(52) U.S. Cl.
CPC ........... *A61M 5/3129* (2013.01); *A61K 33/40* (2013.01); *A61K 41/0038* (2013.01); *A61M 5/3202* (2013.01); *C03C 17/30* (2013.01); *C09D 183/04* (2013.01); *A61M 2205/0238* (2013.01)

(58) Field of Classification Search
CPC .............................. A61K 33/40; A61M 5/3129
See application file for complete search history.

(56) References Cited

U.S. PATENT DOCUMENTS

| | | |
|---|---|---|
| 2,782,100 A | 2/1957 | Greenspan |
| 6,447,610 B1 * | 9/2002 | Vetter .................. A61M 5/3129 118/105 |
| 2002/0127281 A1 | 9/2002 | Tsao |
| 2002/0134965 A1 | 9/2002 | Danjo |
| 2004/0087906 A1 | 5/2004 | Henderson et al. |
| 2006/0009371 A1 | 1/2006 | Wang et al. |
| 2006/0211820 A1 | 9/2006 | Jonn et al. |
| 2008/0071228 A1 * | 3/2008 | Wu .......................... A61L 31/10 604/234 |
| 2010/0010417 A1 * | 1/2010 | Ogawa .................. A61K 9/0009 604/20 |
| 2011/0060290 A1 * | 3/2011 | Bonk ...................... A61P 19/08 604/181 |
| 2013/0236383 A1 | 9/2013 | Klug et al. |
| 2014/0012227 A1 | 1/2014 | Sigg et al. |
| 2014/0147402 A1 | 5/2014 | Klug et al. |
| 2015/0105734 A1 | 4/2015 | Bryant et al. |
| 2019/0262261 A1 | 8/2019 | Ogawa |
| 2020/0016322 A1 | 1/2020 | Takahashi et al. |
| 2020/0022906 A1 | 1/2020 | Ogawa |

FOREIGN PATENT DOCUMENTS

| | | |
|---|---|---|
| CO | 4230164 A | 10/1995 |
| EP | 1281722 A1 | 2/2003 |
| EP | 3378514 A1 | 9/2018 |
| EP | 3437678 A1 | 2/2019 |
| JP | 3-199204 A | 8/1991 |
| JP | 6-9873 A | 1/1994 |
| JP | 2001-061962 A | 3/2001 |
| JP | 2001-276220 A | 10/2001 |
| JP | 2002-088305 A | 3/2002 |
| JP | 2003-201219 A | 7/2003 |
| JP | 2004-509925 A | 4/2004 |
| JP | 2008-535956 A | 9/2008 |
| JP | 2010057597 A | 3/2010 |
| JP | 2011162267 A | 8/2011 |
| JP | 2013-535391 A | 9/2013 |
| JP | 2013-215330 A | 10/2013 |
| KR | 10-2014-0102458 A | 8/2014 |
| RU | 2588531 C1 | 6/2016 |
| WO | 9512482 A1 | 5/1995 |
| WO | 01/57093 A1 | 9/2001 |
| WO | 2008/041514 A1 | 4/2008 |
| WO | 2014187779 A1 | 11/2014 |
| WO | 2017/169038 A1 | 10/2017 |
| WO | 2018215580 A1 | 11/2018 |
| WO | 2018218013 A2 | 11/2018 |

OTHER PUBLICATIONS

Hydrogen Peroxide Material Compatibility, ISM, 2020 (Year: 2020).*
Gates, Journal of Environmental Engineering, Sep. 1995 (Year: 1995).*
Bretschger, 1947 (Year: 1947).*
International Search Report mailed Jun. 16, 2020, issued in International Application No. PCT/JP2020/014110, filed Mar. 27, 2020, 9 pages.
Japanese Office Action mailed Oct. 29, 2019, issued in Japanese Application No. 2019-078110, filed Apr. 16, 2019, 7 pages.
Japanese Office Action mailed Oct. 23, 2019, issued in Japanese Application No. 2019-107223, filed Jun. 7, 2019, 2 pages.
Kusakabe, R., "Production, Properties, and Handling of Hydrogen Peroxide," Japan TAPPI Journal 52(5):22-29, May 1998.
Extended European Search Report mailed Feb. 12, 2021, issued in corresponding Application No. EP20733518.3, filed Mar. 27, 2020, 5 pages.

(Continued)

*Primary Examiner* — Susan T Tran
*Assistant Examiner* — William Craigo
(74) *Attorney, Agent, or Firm* — Mendelsohn Dunleavy, P.C.; Tu A. Phan

(57) ABSTRACT

A syringe that suppresses decomposition of hydrogen peroxide is provided. An object of the present invention is to provide a pre-filled syringe having at least a barrel thereof made of a material having high decomposition capability with respect to hydrogen peroxide, including: a hydrogen peroxide solution therein; and an oil composition applied to an inner wall of the barrel, the oil composition containing silicone oil.

11 Claims, 2 Drawing Sheets

(56) References Cited

OTHER PUBLICATIONS

Russian Office Action, issued Apr. 21, 2022, in corresponding Russian Patent Application No. 2021125153/04, 10 pages.
Examination Report for corresponding Indian application No. 202147043446; dated Aug. 25, 2023 (6 pages).
Office Action for corresponding African Regional application No. AP/P/2021/013517; dated Oct. 3, 2023 (5 pages).
First Office Action for corresponding Chinese application No. 202080021242.2; dated Sep. 21, 2023 (10 pages) Machine Translation.
Columbian Office Action, with English translation, issued Dec. 9, 2022, in corresponding Colombian Patent Application No. NC2021/0014583, 11 pages.
Examination Report No. 1 for corresponding Australian application No. 2023204358; dated Aug. 6, 2024 (7 pages).

* cited by examiner

[Fig. 1]
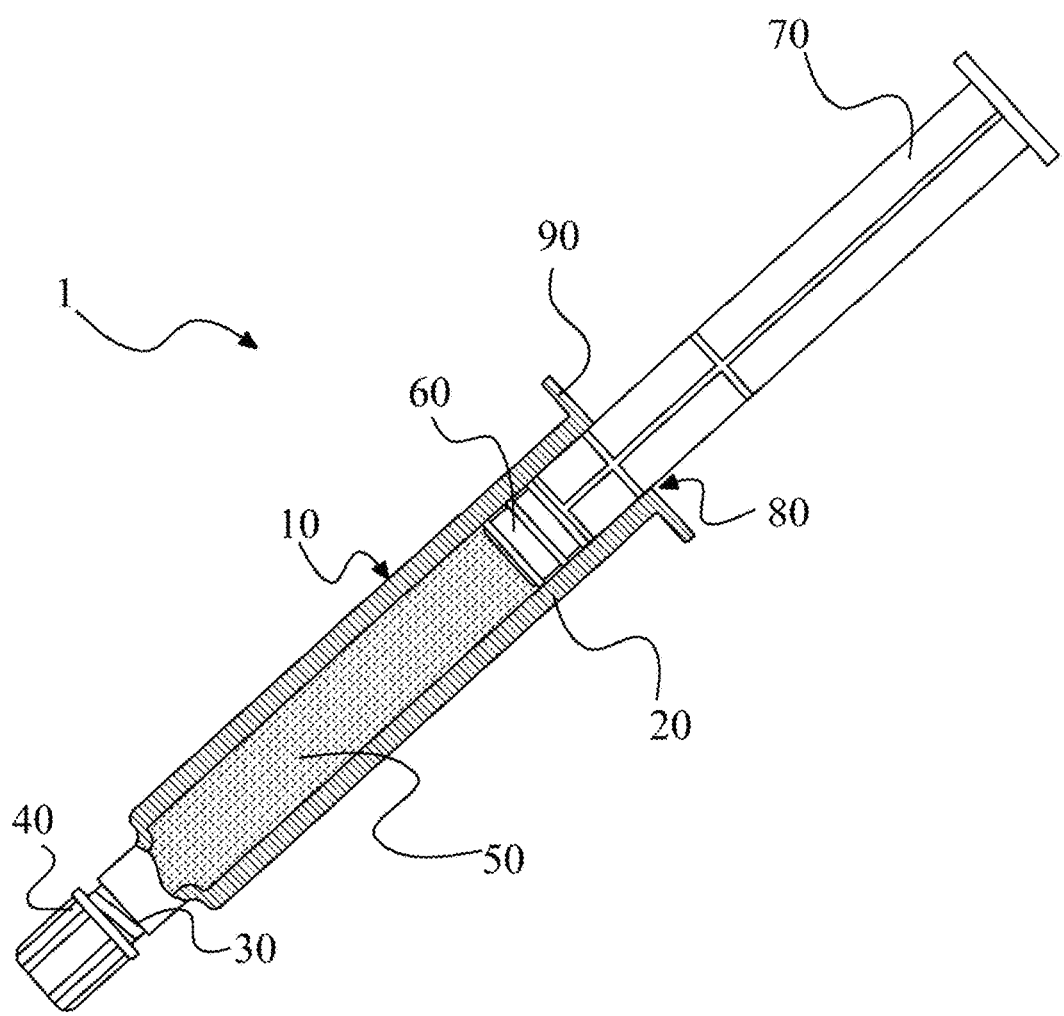

[Fig. 2]
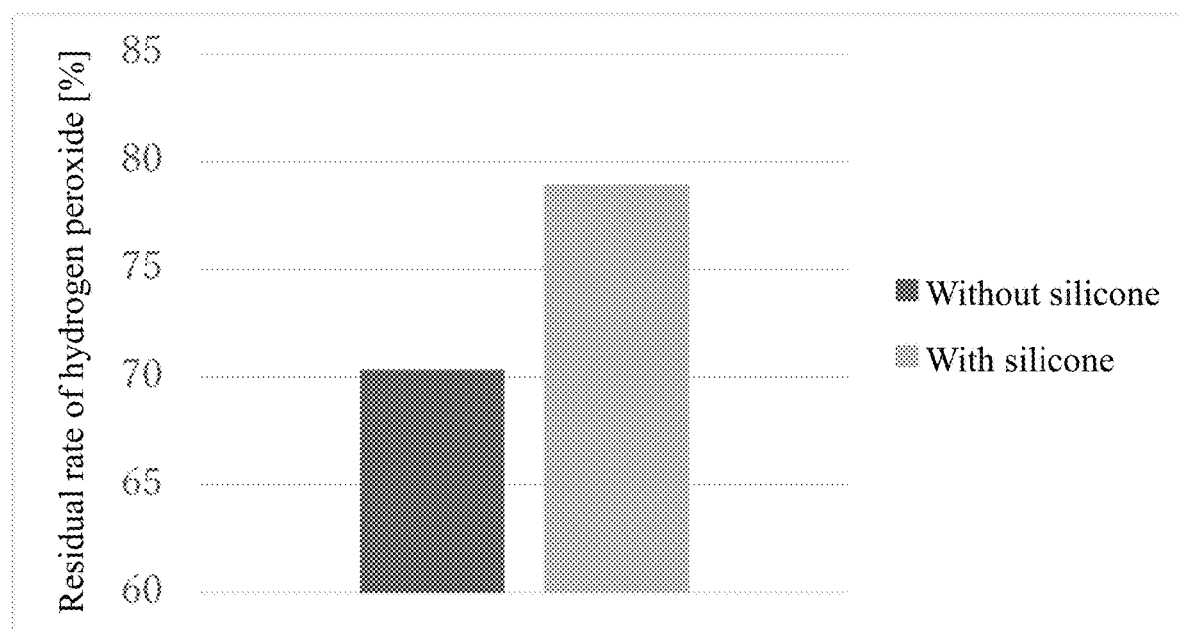

HYDROGEN PEROXIDE SOLUTION-PREFILLED SYRINGE WITH EXCELLENT HYDROGEN PEROXIDE PRESERVATION DUE TO SILICONE OIL INCLUDED IN OIL COMPOSITION

CROSS-REFERENCES TO RELATED APPLICATIONS

This application is a continuation of International Application No. PCT/JP2020/014110, filed Mar. 27, 2020, which claims the benefit of Japanese Application No. 2019-068797, filed Mar. 29, 2019, Japanese Application No. 2019-078110, filed Apr. 16, 2019, Japanese Application No. 2019-107223, filed Jun. 7, 2019, and Japanese Application No. 2019-107227, filed Jun. 7, 2019, the disclosures of which are expressly incorporated herein by reference in their entirety.

TECHNICAL FIELD

The present invention relates to a hydrogen peroxide solution-prefilled syringe with an oil composition containing silicone oil.

BACKGROUND

A hydrogen peroxide solution is used industrially as a bleaching agent, and as a disinfectant in the food industry. A hydrogen peroxide solution containing 2.5 to 3.5% (w/v) hydrogen peroxide (known as "oxydol" in the Japanese Pharmacopoeia) is used for medical purposes as a disinfectant.

This hydrogen peroxide solution can be used as a radiosensitizer by mixing it with a solution of hyaluronic acid or a salt thereof such as sodium hyaluronate in a pre-determined ratio, and then injecting the mixture into a tumor just before the therapeutic radiation dose (Patent Document 1). Decomposition of hydrogen peroxide is accelerated by an increase in liquid temperature thereof due to its thermal decomposition. Non-Patent Document 1 discloses a material suitable for hydrogen peroxide.

PRIOR ART DOCUMENTS

Patent Document

Patent Document 1: WO2008/041514

Non-Patent Document

Non-Patent Document 1: Ryo KUSAKABE, "Production, Properties, and Handling of Hydrogen Peroxide", Japan TAPPI journal, Vol. 52, No. 5, May 1998.

SUMMARY OF THE INVENTION

Problems to be Solved by the Invention

As disclosed in Non-Patent Document 1, there are few types of storage container materials that can be used for storing a hydrogen peroxide solution, and thus there are few choices of materials for the storage container.

Because hydrogen peroxide decomposes rapidly when removed from a special storage container that shields it from light, it must be drawn out in the appropriate volume or weight and then mixed with the sodium hyaluronate solution just before injection, when used as a radiation sensitizer as in Patent Document 1. This places an extra burden on the medical personnel treating the patient. Either the hospital pharmacy must draw out the hydrogen peroxide solution and mix it with the sodium hyaluronate, or a physician must do so at the patient's bedside. In the former case, the pharmacy personnel are burdened and there is risk of delay in transporting the injection mixture from the pharmacy to the patient's bedside. In the latter case, medical personnel at the patient's bedside, who are preparing the patient for radiotherapy, are burdened. In both cases, the complications of drawing out and mixing the solutions increase risks of mistakes that might compromise medical treatment or endanger the patient.

In addition, if the hydrogen peroxide solution is prefilled using a syringe made of conventional glass (for example, borosilicate glass), the glass syringe expands during storage of the hydrogen peroxide solution and the gasket thereof is pushed back. This might interfere with the long-term storage of the hydrogen peroxide solution in such a glass syringe.

Means for Solving the Problems

The present inventor has made intensive studies and found that an oil composition containing silicone oil has an effect of stabilizing the storage of hydrogen peroxide, and thus completed the present invention. In order to solve this problem, the present invention provides a hydrogen peroxide solution pre-filled syringe including an oil composition for stabilizing the storage of hydrogen peroxide.

An object of the present invention is to provide a pre-filled syringe having at least a barrel thereof made of a material having high decomposition capability with respect to hydrogen peroxide, including: a hydrogen peroxide solution therein; and an oil composition applied to an inner wall of the barrel, the oil composition containing silicone oil.

By using the oil composition, it is possible to stabilize storage of hydrogen peroxide in the hydrogen peroxide solution. Thus, by applying the oil composition to the inner wall of the syringe, the hydrogen peroxide solution prefilled in the syringe can be stored for a long time.

Another object of the present invention is to provide an oil composition containing silicone oil, in which the oil composition is for stabilizing storage of hydrogen peroxide and use of the same.

By using the oil composition, it is possible to stabilize storage of hydrogen peroxide in a hydrogen peroxide solution and to store the hydrogen peroxide solution for a long time, regardless of the material of the container or the syringe that stores the hydrogen peroxide solution.

Effect of the Invention

According to the present invention, it is possible to provide the prefilled syringe capable of storing the hydrogen peroxide solution for a long period of time until it can be used as a radiosensitizer.

BRIEF DESCRIPTION OF THE DRAWINGS

FIG. 1 shows a schematic view of a prefilled syringe containing a hydrogen peroxide solution according to the present embodiment.

FIG. 2 shows a graph of residual rates of hydrogen peroxide of each container material in the example.

DESCRIPTION OF THE EMBODIMENTS

Definition

For convenience, certain terms employed in the context of the present disclosure are collected here. Unless defined otherwise, all technical and scientific terms used herein have the same meaning as commonly understood by one of the ordinary skilled in the art to which this invention belongs. The singular forms "a", "and", and "the" are used herein to include plural referents unless the context clearly dictates otherwise.

Notwithstanding that the numerical ranges and parameters setting forth the broad scope of the invention are approximations, the numerical values set forth in the specific examples are described as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

Oil Composition

In the present embodiment, the oil composition contains silicone oil for stabilizing the storage of hydrogen peroxide. The oil composition can be used as an agent for stabilizing the storage of hydrogen peroxide. The oil composition may contain a pharmaceutically acceptable component (such as sterilized water) in addition to the silicone oil. The oil composition can be to be applied to an inner surface of a container or a syringe. The oil composition can suppress decomposition of hydrogen peroxide by a material having high decomposition capability with respect to hydrogen peroxide (e.g., glass, plastic having the high decomposition capability with respect to the hydrogen peroxide such as polyethylene terephthalate, and stainless steel). Thus, a container or a syringe may be made of the material having the high decomposition capability with respect to the hydrogen peroxide.

The silicone oil may have a kinematic viscosity of 20 to 40,000 cSt, preferably 500 to 30,000 cSt, more preferably 800 to 20,000 cSt, and further preferably 1,000 to 15,000 cSt at 25° C.

The kinematic viscosity at 25° C. of the silicone oil can be measured according to JIS Z8803.

Preferably, a linear silicone represented by the following formula (1) can be used as the silicone oil.

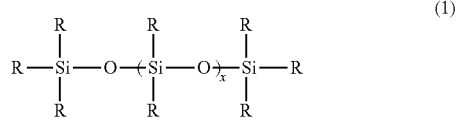

(1)

In the above formula (1), R independently represents an organic functional group not containing a functional group involved in a hydrosilylation reaction such as an alkenyl group or a SiH group, a monovalent hydrocarbon group or a hydroxyl group. R may be the same as or different from each other. x represents an integer of 10 to 1200. R preferably represents an alkyl group or an aryl group, and more preferably represents a methyl group, an ethyl group, or a phenyl group.

The linear silicone represented by the above formula (1) includes polydiorganosiloxane having both ends blocked with triorganosilyl groups, which is preferably polydialkylsiloxane, polydiarylsiloxane, polyalkylarylsiloxane, or a copolymer thereof, more preferably polydimethylsiloxane or polymethylphenylsiloxane, further preferably polydimethylsiloxane in which R are all methyl groups.

Syringe

FIG. 1 shows a schematic diagram of a prefilled syringe (1) filled with hydrogen peroxide solution (50) according to the present embodiment. In the present embodiment, a syringe (10), particularly a barrel (20) of the syringe (10), has generally cylindrical shape. In the present embodiment, the syringe (10) has, at one end thereof, a needle mounting part (30) from which the hydrogen peroxide solution (50) is discharged. In the present embodiment, the syringe (10) has, at the other end thereof, an opening (80) for inserting a plunger rod (70). In the present embodiment, the syringe (10) has a flange (90) provided around the opening (80). In the prefilled syringe (1) shown in FIG. 1, a silicone oil is applied to an inner wall of the syringe (10). In order to seal the filled hydrogen peroxide solution (50), the prefilled syringe (1) shown in FIG. 1 has a cap (40) provided on the needle mounting part (30) and the plunger rod (70) inserted from the opening (80), the plunger rod (70) having a gasket (60).

In the present embodiment, the syringe for hydrogen peroxide solution means a syringe having a low decomposition capability with respect to the hydrogen peroxide in the hydrogen peroxide solution. In the present embodiment, the hydrogen peroxide solution means a solution in which a solvent (for example, water) contains hydrogen peroxide and if necessary, additives (for example, phosphoric acid and phenacetin). In the present embodiment, the syringe may be manufactured from a single material or may be made with a plurality of materials (including a multilayer structure such as a coating). In the case of a syringe manufactured from the single material, the entire syringe is made of a material having high decomposition capability with respect to hydrogen peroxide (e.g., glass, plastic having the high decomposition capability with respect to the hydrogen peroxide such as polyethylene terephthalate, and stainless steel). In the case of a syringe made with a plurality of materials, aside from the part where an inner wall of the syringe is made of glass, the remaining parts may be made of a material having high or law decomposition capability with respect to hydrogen peroxide. However, all parts of the inner wall of the syringe need to be made of the material having the high decomposition capability with respect to the hydrogen peroxide. Thus, main parts, such as the inner surface of the barrel of the syringe, need to be made of the material having the high decomposition capability with respect to the hydrogen peroxide. In other words, parts that may come into contact with the hydrogen peroxide solution, such as a plunger rod, luer lock, cap and gasket, need to be made of the material having the high decomposition capability with respect to the hydrogen peroxide. In the present embodiment, the syringe may be for a radiosensitizer.

The decomposition capability of hydrogen peroxide can be determined from the ratio of the concentration of hydrogen peroxide in the hydrogen peroxide solution after start of storage to the concentration of hydrogen peroxide in the hydrogen peroxide solution before the start of the storage under specific temperature condition (residual rate of hydrogen peroxide). The storage is performed in a sealed state. The temperature condition is not limited, but may be 35° C., 37° C., 40° C., or 60° C. A period of the storage is not limited, but may be one week, two weeks, three weeks, or four weeks, or four weeks or more. The concentration of hydrogen peroxide in the hydrogen peroxide solution before the start of the storage may be any concentration, for example in the range of 0.01 to 40% (w/v). In an embodiment, the decomposition capability of hydrogen peroxide to the plastic is lower than that of a glass. The residual rate of hydrogen peroxide in the plastic may be 70% or more, preferably 75% or more, more preferably 78% or more, still more preferably 80% or more under the condition that a solution containing 2.5 to 3.5% (w/v) hydrogen peroxide is hermetically stored at 60° C. for 4 weeks. The amount of hydrogen peroxide in the hydrogen peroxide solution can be determined by titration with a potassium permanganate solution according to an oxydol determination method described in Japanese Pharmacopoeia.

In the present embodiment, the syringe is provided as a hydrogen peroxide solution pre-filled syringe. The hydrogen peroxide solution pre-filled syringe includes a gasket slidably provided with the syringe. Furthermore, a needle mounting portion of the hydrogen peroxide solution pre-filled syringe is sealed with, for example, a cap or the like.

In the present embodiment, the concentration of hydrogen peroxide in the hydrogen peroxide solution in the prefilled syringe is, for example, 0.01, 0.02, 0.03, 0.04, 0.05, 0.06, 0.07, 0.08, 0.09, 0.1, 0.5, 1, 5, 10, 15, 20, 25, 30, 35 or 40%, or may be in the range between any two of the numerical values exemplified herein, for example, 0.01 to 40% (w/v), preferably, 0.05 to 30% (w/v).

Application

The oil composition according to the present embodiment can be applied using a spray or the like. Upon the application, the oil composition may be dissolved in a suitable solvent. When applying the oil composition to the inner wall of the syringe, the oil composition can be applied to the inner wall of the syringe at an application amount of 0.02 to 0.2 mg/cm$^2$ by spraying. After the application to the inner wall of the syringe, the oil composition may be made uniform in thickness thereof by using a device such as a squeegee or by softening the silicone oil in the oil composition by a heat treatment (for example, an autoclave treatment).

EXAMPLE

Hydrogen Peroxide Solution Stability Test

Stability test of a hydrogen peroxide solution was performed using a glass container coated with silicone oil and a glass container not coated with the silicone oil. The silicone oil was purchased from Dow Corning (product name: Dow Corning 360 Medical Fluid (12,500 cSt)). The hydrogen peroxide solution was added to each container, sealed, and then stored at 60° C. for 4 weeks. The residual rates of hydrogen peroxide in the hydrogen peroxide solutions after storage were measured. Oxydol "KENEI" (containing 2.5 to 3.5% (w/v) hydrogen peroxide, phosphoric acid and phenacetin) manufactured by Kenei Pharmaceutical Co., Ltd. was used as the hydrogen peroxide solution. The amount of hydrogen peroxide in the hydrogen peroxide solution was detected by titration with a potassium permanganate solution according to oxydol determination method described in the Japanese Pharmacopoeia. The results are shown in FIG. 2.

In the case of the glass container not coated with the silicone oil, the residual ratio of hydrogen peroxide was about 70%. The residual ratio of the glass container coated with the silicone oil was 78% or more. As a result, the glass container coated with the silicone oil was able to suppress the decomposition of hydrogen peroxide more than the glass container not coated with the silicone oil.

EXPLANATION OF REFERENCES

1 Prefilled syringe
10 Syringes
20 Barrel
30 Needle mounting part
40 Cap
50 Hydrogen peroxide solution
60 Gasket
70 Plunger rod
80 Opening
90 Flange

The invention claimed is:

1. A pre-filled syringe capable of storing a hydrogen peroxide solution used as a radiosensitizer comprising:
    a barrel having an oil composition applied to an inner wall of the barrel, the oil composition containing silicone oil having a kinematic viscosity of from 20 to 30,000 cSt at 25° C.,
    the hydrogen peroxide solution filled in the barrel,
    a needle mounting part provided at one end of the syringe that is sealed, and
    a plunger rod having a gasket at the other end of the syringe to seal the hydrogen peroxide solution filled in the barrel,
    wherein the pre-filled syringe is capable of storing the hydrogen peroxide solution for at least four weeks at 60° C., and
    the concentration of hydrogen peroxide in the hydrogen peroxide solution is from 2.5% to 3.5% (w/v).

2. The pre-filled syringe according to claim 1, wherein the silicone oil is a linear silicone represented by the following formula (1):

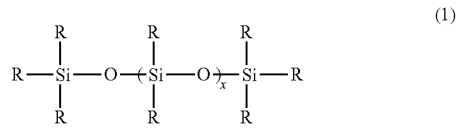

wherein, in the above formula (1),
    R independently represents a monovalent hydrocarbon group, a hydroxyl group,
    or an organic functional group not containing a functional group involved in a hydrosilylation reaction,
    R may be the same or different from each other, and
    X represents an integer of 10 to 1200.

3. The pre-filled syringe according to claim 2, wherein R independently represents an alkyl group or an aryl group.

4. The pre-filled syringe according to claim 3, wherein R independently represents a methyl group, an ethyl group, or a phenyl group.

5. The pre-filled syringe according to claim 2, wherein the linear silicone represented by the above formula (1) is polydiorganosiloxane having both ends blocked with triorganosilyl groups.

6. The pre-filled syringe according to claim 5, wherein the polydiorganosiloxane is polydialkylsiloxane, polydiarylsiloxane, polyalkylarylsiloxane, or a copolymer thereof.

7. The pre-filled syringe according to claim 6, wherein the polydialkylsiloxane is polydimethylsiloxane or polymethylphenylsiloxane.

8. The pre-filled syringe according to claim 7, wherein the polydialkylsiloxane is polydimethylsiloxane, and R are all methyl groups.

9. The syringe according to claim 1, wherein the pre-filled syringe is a glass syringe.

10. The syringe according to claim 1, wherein the needle mounting part is sealed with a cap.

11. The syringe of claim 1, wherein the hydrogen peroxide solution is characterized by a residual rate of hydrogen peroxide of greater than 70% after the period of at least four weeks at 60° C.

* * * * *